United States Patent [19]

Toyoda et al.

[11] Patent Number: 5,763,591
[45] Date of Patent: Jun. 9, 1998

[54] POLYNUCLEIC ACID SEQUENCES THAT ARE FUNCTIONALLY ASSOCIATED WITH THE DEVELOPMENT OF AUTOIMMUNE DISEASE

[75] Inventors: Hiroo Toyoda, Arcadia; Bent Formby, Santa Barbara, both of Calif.

[73] Assignee: Cedars-Sinai Medical Center, Los Angeles, Calif.

[21] Appl. No.: 621,502

[22] Filed: Mar. 25, 1996

[51] Int. Cl.⁶ .......................... C07H 21/02; C07H 21/04
[52] U.S. Cl. .................. 536/23.1; 536/23.5; 536/24.3; 536/24.31; 536/24.33; 536/25.22; 530/300; 530/350; 435/252.3
[58] Field of Search .................... 536/23.1, 24.3, 536/23.5, 24.31, 24.33, 25.32; 435/252.3; 530/300, 350

[56] References Cited

U.S. PATENT DOCUMENTS

| | | |
|---|---|---|
| 4,623,619 | 11/1986 | Owerbach et al. . |
| 5,039,606 | 8/1991 | Nepon . |
| 5,059,519 | 10/1991 | Owerbach . |
| 5,310,893 | 5/1994 | Erlich et al. . |

FOREIGN PATENT DOCUMENTS

| | | |
|---|---|---|
| WO 88/02783 | 4/1988 | WIPO . |
| WO 89/04875 | 6/1989 | WIPO . |
| WO 92/04632 | 3/1992 | WIPO . |
| WO 93/09141 | 5/1993 | WIPO . |

OTHER PUBLICATIONS

D. Raum, et al., 1 (8128):1208–10 *Lancet* (1979).
D. Stetler, et al., 82(23):8100–4 *Proc. Natl. Acad. Sci. USA* (Dec. 1985).
B. Michelsen, et al., 79(4):114–52 *J. Clin. Invest.* (1987).
J.A. Todd, et al., 4(5):129–34 *Trends Genet.* (1988).
C. Julier, et al., 354:155–159 *Nature* (Nov. 1991).
P. Rubinstein, 30:270–7 *Human Immunology* (1991).
T. Hawkins, et al., 202:201–5 *Proc. Soc. Exp. Biol. Med.* (1993).
H.S. Fox, 175:1409–12 *J.Exp. Med.* (1992).
J.A. Todd, et al. 41:1029–34 *Diabetes* (1992).
J.A. Todd, 14(1):33–58 *Springer Semin. Immunopathol.* (1992).
P. Patel, et al., 36(4):264–5 *Immunogenetics* (1992).
S.C. Bain, et al., 2:212–15 *Nat. Genet.* (1992).
A.M. Lucassen, et al., 4:305–10 *Nat. Genet.* (1993).
D. Owerbach, et al., 42:1708–14 *Diabetes* (1993).
H. Ikegami, et al., 20(1):7–10 *Diabetes Res. Clin. Pract.* (1993).
K. Chesnut, et al., 4:549–54 *Mamm. Genome* (1993).
J.L. Davies, et al., 371:130–136 *Nature* (1994).
L. Hashimoto, et al., 371:161–64 *Nature* (1994).
L. Leigh Field, et al., 8:189–94 *Nat. Genet.* (1994).
S.T. Bennett, et al., 9:284–92 *Nat. Genet.* (1995).
Kennedy, et al., 9:293–98 *Nat. Genet.* (1995).
Ito et al *Science* vol. 249 (1990) pp. 790–793.
Chen et al *Journal of Lipid Research* vol. 35 (1994) pp. 1918–1924.

*Primary Examiner*—Marian C. Knode
*Assistant Examiner*—Heather Bakalyar
*Attorney, Agent, or Firm*—Viviana Amzel; Pretty, Schroeder & Poplawski

[57] ABSTRACT

The present invention provides polynucleic acid sequences that are functionally associated with autoimmune diseases, such as, for example, insulin-dependent diabetes mellitus. Significantly, quantities of transcriptional and translational product encoded by the invention polynucleic acid sequences are elevated in mammals having a predisposition to autoimmune disease, as compared to their quantities in normal mammals. In accordance with the present invention, there also are provided polypeptides encoded by the invention polynucleic acid sequences, antibodies that are capable of binding to the invention polypeptides, as well as methods and kits for screening for autoimmune diseases.

43 Claims, 1 Drawing Sheet

5,763,591

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 358 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Non-Obese Diabetic Mouse
        ( F ) TISSUE TYPE: Splenocyte ( x i ) SEQUENCE DESCRIPTION: SEQ ID NO:1:

```
GCTTCTTGAT  TGCCAATAAC  ATGCAGATGT  ACATTATTTA  ATTGACCCAT  GTTCTGGTTA      60

TCATTCGGTA  AACTGTAGCA  AGCTTCAACA  TTGAACTCTT  AGAAGCCTCT  GCCATAGACC     120

TTCCACTGGG  GTGAGAAAGG  CAGCTTTGAC  CTTAGCTCAG  GCGAGCACCC  CCAGGACTGC     180

CATATGGGGA  GCCAGGTAGA  ACCTCAACCC  TGCATGTTCC  CACCCTAGGT  CCCCCTCCTC     240

CTTGCCTCCA  CCACATACCT  TGAACCACCA  ATTCTGCAGT  GGAAGTAGCT  CTTCAACGCT     300

GTTGGTGGCA  TTTACAGAAT  AGGTCCCGGA  GTCTTCAGGG  TATGCTTCGG  CAATCAAG      358
```

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:2:

CTTGATTGCC         10

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:3:

CATTTTTTT TTT         13

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:4:

CTGTAGCAAG CTTCAACATT G         21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:5:

AAGGTATGTG GTGGAGGCAA G         21

( 2 ) INFORMATION FOR SEQ ID NO:6:

( i ) SEQUENCE CHARACTERISTICS:
        ( A ) LENGTH: 439 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
    ( F ) TISSUE TYPE: Splenocyte ( i x ) FEATURE:
    ( A ) NAME/KEY: CDS
    ( B ) LOCATION: 1..27
    ( D ) OTHER INFORMATION: /partial
        / label= polypeptide ( x i ) SEQUENCE DESCRIPTION: SEQ ID NO:6:

| | | | | | | | | | | |
|---|---|---|---|---|---|---|---|---|---|---|
| ATT | CCA | CGG | CCT | ACA | TGT | GGA | CAT | TTC | TAAATTTTCC TACCTTTTTC | 47 |
| Ile | Pro | Arg | Pro | Thr | Cys | Gly | His | Phe | | |
| 1 | | | | 5 | | | | | | |

```
AGTTTTCCTC GCCATATTTC ACGTCCTAAA GTGTGTATTT CTCATTTTCC TGTGATTTTC      107
AGTTTTCTCG CCATATTCCA AGGTTCCTTC AGTGTGCATT TCTCATTTTT CACGTTTTTT      167
AGTGATTTTG CATTTTTCAA GTCGTCAAGT GGATGTTTCT CATTTTCCAT GATTTTCAGT      227
TTTCTTGCCA TATTCCAAGT CCTACAGTGG ACATTCTAA  ATTTTCCACC TTTTTCAGTT      287
TTCCTCGCCA TATTTCACGT GCTAAAGTGT GTATTTCTCA TTTTCGTGA  TTTTCAGTTT      347
TCTCGCCATA TTCCAGGTCC TTCAGTGTGC ATTTCTCATC TTTCACGTTT TTAGTGATT       407
TCGTCATTTT TCGAGTCTTC AGGGTATGCT TC                                    439
```

( 2 ) INFORMATION FOR SEQ ID NO:7:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

Ile Pro Arg Pro Thr Cys Gly His Phe
 1               5

( 2 ) INFORMATION FOR SEQ ID NO:8:

( i ) SEQUENCE CHARACTERISTICS:
    ( A ) LENGTH: 461 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( v i ) ORIGINAL SOURCE:
    ( F ) TISSUE TYPE: Splenocyte ( x i ) SEQUENCE DESCRIPTION: SEQ ID NO:8:

```
ACTCACTATA GGGCTCGAGC GGCCGCCCGG GCAGGTGTGG ACATTGCTAA ATTTTCCACC      60
TTTTTCAGTT TTCCTCGCCA TATTTAACGT CCTAAAGTGT GTATTTCTCA TTTTCCGTGA     120
TTTTCAGTTT TCTCGCCATA TTCCAGGTTC TTCAGTGTGC ATTTCTCACT TTTCACGTTT     180
TTAGTGATT  TCGTCATTTT CCAAGTCGTC AAGTGGATGT TTCTCATTTT CCATGATTTT     240
CAGTTTTCTA GCCATATTCC ACGGTCCTAC AGTGGACATT CTAAATTTT  CCTACCTTTT     300
TCAGTTTTCC TCGCCATATT TCACGTCCTA AAGTGTGTAT TTCTCATTTT CTGTGATTTT     360
CAGTTTTCTC GCATATTCCA GGTCCTTCAG TGTGCATTTC TCATTTTTC ACGTTTTTA       420
GTGATTTCGT CATTTTTCAA GTCGTCAAGT GGAATGTTTC T                         461
```

( 2 ) INFORMATION FOR SEQ ID NO:9:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( x i ) SEQUENCE DESCRIPTION: SEQ ID NO:9:

ATGGATGACG ATATCGCT                                                18

( 2 ) INFORMATION FOR SEQ ID NO:10:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( x i ) SEQUENCE DESCRIPTION: SEQ ID NO:10:

ATGAGGTAGT CTGTCAGGT                                               19

POLYNUCLEIC ACID SEQUENCES THAT ARE FUNCTIONALLY ASSOCIATED WITH THE DEVELOPMENT OF AUTOIMMUNE DISEASE

FIELD OF THE INVENTION

The present invention relates to polynucleic acid sequences that are functionally associated with the development of autoimmune diseases, such as, for example, insulin-dependent diabetes mellitus. Significantly, levels of transcriptional and translational products encoded by the invention polynucleic acid sequences are elevated in mammals having a predisposition to developing autoimmune disease, as compared to their levels in normal mammals. The present invention also relates to methods and kits for screening for autoimmune diseases, as well as therapeutic methods for inhibiting the onset of autoimmune disease.

BACKGROUND OF THE INVENTION

Diabetes mellitus is a chronic, incurable disease that is characterized by insufficient insulin secretion, hyperglycemia and a propensity to develop universal microangiopathy, neuropathy and atherosclerosis. It is a common condition that afflicts 1 to 2 percent of Caucasian populations. Insulin-dependent diabetes mellitus (IDDM) is a type of diabetes mellitus that afflicts 10 to 15 percent of all diabetes mellitus sufferers. IDDM is a multifactorial disease characterized by selective pancreatic beta cell destruction, a generally low age at onset, and a high percentage of autoantibodies directed against antigenic determinants of the beta-cells. With a peak age-at-onset of 12 years, IDDM is one of the fastest growing childhood diseases, with an incidence ranging from 5 to 35 per 100,000 per year in Caucasians of European descent.

The characteristic destruction of pancreatic beta cells caused by IDDM results in very low, if any, insulin secretion, which if left untreated, can lead to hyperglycemia, diabetic acidosis, and diabetic coma. There are also complications associated with IDDM. These complications include retinopathy, glaucoma, and cardiovascular disease. Exogenous insulin must be taken by IDDM sufferers to control the diabetes.

The pathogenesis of IDDM involves autoimmune phenomena, such as the occurrence of insulitis and the presence of islet cell autoantibodies. However, the specific cause of IDDM is yet unknown. Although diagnosis of IDDM is typically made on the basis of clinical observations (e.g., excessive thirst, elevated levels of sugar in blood and urine, and in more advance cases, acetone in the urine, among others), Michelsen, et al. have reported that IDDM actually appears long before clinical onset, evolving after immune abnormalities are present. *J. Clin. Invest.*, 79(4):1144 (1987). Unfortunately, diagnostic procedures for detecting these abnormalities have not yet been made available.

Although IDDM has been observed to run in families, efforts to identify a genetic basis for IDDM (i.e., one on which a diagnostic test for IDDM can be based) have been met with limited success. For example, although it has been reported that almost all IDDM patients carry antigens for HLA-DR3 and/or HLA-DR4, the frequency of HLA-DR specificity in the general population alone is fairly high (i.e., nearly 60%). Thus, identification of HLA specificity is insufficient, by itself, to predict the development of IDDM.

Identification of polynucleic acid sequences that are associated with the development of IDDM would represent a significant advance, not only towards development of new diagnostic and therapeutic methods related to IDDM, but possibly other autoimmune diseases as well. Patients with IDDM, as well as their relatives, have been reported to have an increased risk for developing other autoimmune diseases, such as autoimmune thyroid disease, Addison's disease, pernicious anemia, vitiligo, and myasthenia gravis. See Rotter, et al., "Diabetes Mellitus" (Chapter 21) in "The Genetic Basis of Common Diseases," (eds. King, et al.), Oxford monographs on Medical Genetics, No. 20, 422–23, Oxford University Press, New York (1992).

Accordingly, it would be highly desirable to identify polynucleic acid sequences that are associated with the occurrence of autoimmune diseases, for use as a tool in diagnosis, as well as to help facilitate the further elucidation of the pathology of these diseases.

BRIEF DESCRIPTION OF THE INVENTION

The present invention provides polynucleic acid sequences that are functionally associated with the development of autoimmune diseases, in particular, insulin-dependent diabetes mellitus. The polynucleic acid, peptide, polypeptide and protein products encoded by these sequences are produced at elevated levels in mammals having a predisposition for autoimmune diseases, as compared to their levels in normal mammals. The invention also provides polypeptides encoded by the invention sequences, as well as antibodies that are capable of binding to the invention polypeptides. In addition, methods and kits for screening for autoimmune disease are also provided. Accordingly, the invention has utility in the diagnosis and prevention of autoimmune disease.

DETAILED DESCRIPTION OF THE INVENTION

Figure 1:
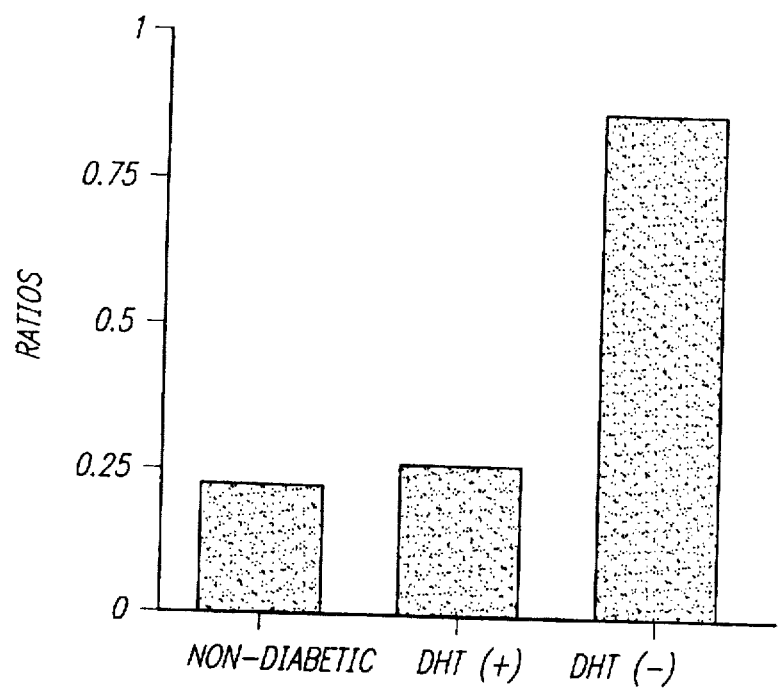
FIG. 1 illustrates the differential quantities of cDNA of the present invention associated with mRNA obtained from: (1) splenocytes from 3 to 5 week old, female non-diabetic (i.e., prior to onset of insulitis), non-obese diabetic (NOD) mice; (2) splenocytes from 14 to 16 week old, 5-α-dihydrotestosterone(5-DHT)-treated female NOD mice; and (3) splenocytes from 14 to 16 week old, untreated prediabetic (i.e., after onset of advanced insultis), female NOD mice. For each splenocyte sample, the quantity of cDNA associated with mRNA transcribed from polynucleic acid of the present invention (i.e., invention cDNA) is expressed as a ratio of the optical density of invention cDNA to the optical density of cDNA associated with mRNA transcribed from control gene, α-actin gene, in the same sample.

In accordance with the present invention, there are provided polynucleic acid sequences wherein products encoded thereby are produced at elevated levels in mammals having a predisposition to autoimmune disease, as compared to their levels in normal mammals. The terms "polynucleic acid," "polynucleotide" and "nucleic acid" refer herein to deoxyribonucleic acid ("DNA") and ribonucleic acid ("RNA") in all their forms, i.e., single and double-stranded DNA, cDNA, mRNA, and the like. As used herein, the term "encode" in its various grammatical forms includes nucleotides and/or amino acids which correspond to other nucleotides or amino acids in the transcriptional and/or translational sense. The term DNA refers to deoxyribonucleic acid in all of its forms, i.e., single- and double-stranded genomic and complementary DNA. The term "encoded products" embraces transcriptional products and complements thereof, translational products, as well as fragments and derivatives thereof, all of which are derived from the invention sequences.

The phrase "autoimmune disease" refers herein to a disease produced when the body loses its normal tolerance for its own antigenic markers on its cells. Autoantibodies are produced by B lymphocytes and attack normal cells whose surface contains a "self" antigen or autoantigen causing destruction of tissue. Diabetes mellitus, in which autoantibodies attack the insulin-producing cells of the pancreas, is one autoimmune disease. Other autoimmune diseases contemplated for diagnosis and treatment by the present invention include rheumatoid arthritis (caused by inflammatory changes in the connective tissue of joints), multiple sclerosis (caused by autoantibody destruction of the myelin sheath covering nerves), and the like. Hemolytic anemia, some forms of glomerulonephritis, myasthenia gravis, Reiter's syndrome, Graves' disease, Sjogrens disease, autoimmune thyroid disease, vitiligo, and systemic lupus erythematosus are also considered to be autoimmune diseases, and are therefore also contemplated for diagnosis and treatment by the present invention.

As used herein, the phrase "mammals having a predisposition to autoimmune disease" refers to mammals that will likely develop autoimmune disease at some future time in their lives, unless prior mortality intervenes.

Polynucleic acids contemplated to be within the scope of the present invention encode products that are produced at elevated levels in mammals having a predisposition to autoimmune disease, as compared to normal mammals (i.e., mammals that do not have a predisposition to autoimmune disease). Such polynucleic acids include, for example, DNA sequences having the same, or substantially the same sequences as the exemplary DNA sequences set forth in SEQ ID NO 1, SEQ ID NO 6, SEQ ID NO 8, and the 1.6 kilobase pair ("kb") polynucleic acid sequence which was isolated as described in "Example 6," set forth below. The 1.6 kb polynucleic acid sequence was inserted into plasmid pDHINOD1, deposited with the American Type Culture Collection as of Mar. 14, 1996, and assigned ATCC Accession No. 97479. Also contemplated are polynucleic acid sequences that encode a polypeptide having the same, or substantially the same sequence as the amino acid sequence set forth in SEQ ID NO 7.

As used herein, the phrase "substantially the same," when used in conjunction with nucleic acid sequences, refers to nucleic acid sequences having non-consequential substitutions as compared to the reference sequence. For example, if the polynucleic acid sequences encode a protein, the substitutions in polynucleic acid sequences that do not substantially alter the function of the protein it encodes, or the tertiary structure of that protein, would be considered to produce a polynucleic acid sequence that is substantially the same as the reference sequence.

When the phrase "substantially the same" is used in conjunction with amino acid sequences, it refers to amino acid sequences that result from substitutions that do not substantially alter the function of the protein or its tertiary structure. For example, substitution of a charged amino acid residue for a similarly charged amino acid residue or substitution of a non-polar amino acid residue for another non-polar amino acid residue would typically be considered to produce an amino acid sequence that is substantially the same as the reference sequence.

The polynucleic acid sequence set forth in SEQ ID NO 1 is 358 base pairs ("bp") in length and is the sequence of a partial clone that was isolated as described in the "Examples" set forth below. Sequence searches conducted in GenBank indicate that the polynucleic acid sequence set forth in SEQ ID NO 1 is a novel DNA sequence. SEQ ID NO 1 appears to encode a carboxy-terminal amino acid sequence (extending from base pair number 1 to base pair number 6) followed by a 3' untranslated sequence containing 352 nucleic acid residues. The polynucleic acid set forth in SEQ ID NO 1, and fragments thereof, can be used as probes.

The polynucleic acid sequences set forth in SEQ ID NO 6 and SEQ ID NO 8 are partial sequences derived from a 1.6 kb cDNA clone that was isolated as described in the "Examples" set forth below. Sequence searches conducted in GenBank indicate that the polynucleic acid sequences set forth in SEQ ID NO 6 and SEQ ID NO 8 are also novel DNA sequences.

The sequence set forth in SEQ ID NO 6 is a partial sequence of the 3' end of the isolated 1.6 kb cDNA clone. SEQ ID NO 6 contains 439 nucleic acid residues and an open reading frame that extends from base pair number 1 to base pair number 27. Set forth in SEQ ID NO. 7 is the deduced amino acid sequence encoded by the sequence extending from base pair number 1 to base pair number 27 of SEQ ID NO. 6.

The sequence set forth in SEQ ID NO 8 is a partial sequence of the 5' end of the isolated 1.6 kb cDNA clone. SEQ ID NO 8 contains 461 nucleic acid residues.

Plasmids identified as "pDHTNOD1," containing the isolated 1.6 kb polynucleic acid sequence have been deposited as of Mar. 14, 1996, with the American Type Culture Collection (ATCC), 12301 Parklawn Drive, Rockville, Md. 20852, and assigned ATCC Accession No. 97479. The deposit has been made under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and other nations or international organizations in which this application, or an application claiming priority of this application, is filed or in which any patent granted on any such application is granted. In particular, upon issuance of a U.S. patent based on this or any application claiming priority to or incorporating this application by reference thereto, all restriction upon availability of the deposited material will be irrevocably removed.

A detailed description of the experimental methods used to identify and isolate polynucleic acid sequences of the present invention and the methods used to identify their functional association with autoimmune disease development is provided in the "Examples" set forth below.

As used herein, the term "elevated level" refers to the relative quantity of encoded product (e.g., polynucleic acid, proteins, polypeptides, peptides, and the like) of invention polynucleic acids in mammals having a predisposition to autoimmune diseases, as compared to the quantity of encoded product of invention polynucleic acids in normal mammals.

The phrase "functional association" refers herein to the relationship between the production levels of encoded products of invention polynucleic acids and the development of autoimmune disease. As described herein, polynucleic acids of the present invention are functionally related to development of autoimmune disease because products encoded by invention polynucleic acids are produced (i.e., by transcription and translation) at elevated levels in mammals predisposed to autoimmune disease, as compared to their levels of production in normal mammals.

As contemplated in the practice of the present invention, production of encoded products of invention polynucleic acids is elevated in mammals having a predisposition to autoimmune disease to a level of at least about two times that in normal mammals. Preferably, production of encoded products of invention polynucleic acids is elevated to a level of at least about three times that in mammals having a predisposition to autoimmune disease, as compared to production levels in normal mammals. Most preferably, production of encoded products of the invention polynucleic acids is elevated to a level of at least about four times that in mammals having a predisposition to autoimmune disease, as compared to production levels in normal mammals.

As used herein, the term "normal" refers to mammals that are not susceptible to autoimmune disease, and more specifically, mammals that are free from any clinical symptoms associated with autoimmune disease. Normal mammals can be identified on the basis of a clinical diagnosis by a physician or veterinarian having ordinary skill in the diagnosis of autoimmune disease.

Quantitation of the relative levels of production of encoded products associated with invention polynucleic acids in normal and test subject mammals can be accomplished using methodologies that are well known in the art, such as, for example, polymerase chain reaction methodologies (including, for example, competitive PCR as described in Andus, et al., *Regional Immunology,* 5:11–17 (1993), incorporated herein by reference). The quantity of encoded products can be readily determined using techniques that are well known to those having ordinary skill in the art. See, e.g., Sambrook et al., Molecular Cloning: A Laboratory Manual, Second Edition, Cold Spring Harbor (1989), incorporated herein by reference. Exemplary methods include optical density measurements, autoradiography, and the like, for quantifying levels of polynucleic acid; and ELISA, High Pressure Liquid Chromatography (HPLC), Western Blotting, and the like, for quantifying levels of polypeptides.

The invention further relates to autoimmune indicating nucleotide probes that are sufficiently complementary to the above-described polynucleic acid to hybridize thereto, preferably under high stringency conditions. The term "autoimmune indicating nucleotide probes" refers herein to nucleotide probes that indicate the presence of polynucleic acids that are functionally associated with autoimmune disease predisposition. Exemplary probes include oligomers that are at least about 20 to 25 nucleic acid residues long and that are selected from any 20 to 25 or more contiguous residues of polynucleic acids of the present invention. Preferably, oligomeric probes used in the practice of the present invention are at least about 40 nucleic acid residues long and selected from any 40 or more contiguous residues of polynucleic acids of the present invention. More preferably, oligomeric probes used in the practice of the present invention are at least about 60 nucleic acid residues long and that are selected from any 60 or more contiguous residues of polynucleic acids of the present invention. The present invention also contemplates oligomeric probes that are 150 nucleic acid residues long or longer. Those of ordinary skill in the art realize that nucleic acid probe technology is well known and that suitable hybridization conditions for achieving the hybridization of a probe of a particular length to polynucleic acids of the present invention can readily be determined. Such manipulations to achieve optimal hybridization conditions for probes of varying lengths are well known in the art. See, e.g., Sambrook et al., *Molecular Cloning: A Laboratory Manual,* Second Edition, Cold Spring Harbor (1989), incorporated herein by reference.

Preferably, oligomeric probes of the present invention are labeled to render them readily detectable. Detectable labels may be any species or moiety which may be detected either visually or with the aid of an instrument. Commonly used detectable labels are radioactive labels, such as, for example, $^{32}P$, $^{14}C$, $^{125}I$, $^{3}H$, $^{35}S$, and the like. Biotin labeled nucleotides can be incorporated into DNA or RNA by such techniques as nick translation, chemical and enzymatic means, and the like. The biotinylated probes are detected after hybridization using indicating means such as avidin/streptavidin, fluorescent labeling agents, enzymes, colloidal gold conjugates, and the like. Nucleic acids may also be labeled with other fluorescent compounds, with immunodetectable fluorescent derivatives, with biotin analogues, and the like. Nucleic acids may also be labeled by means of attachment to a protein. Nucleic acids crosslinked to radioactive or fluorescent histone single-stranded binding protein may also be used. Those having ordinary skill in the art recognize that there are other suitable methods for detecting oligomeric probes and other suitable detectable labels available for use in the practice of the present invention.

In another embodiment, the present invention relates to constructs that include an invention polynucleic acid, an origin of replication, and a promoter. The constructs of the invention are useful to introduce invention polynucleic acid sequences into cells for expression and/or replication. Selection and use of such constructs are well known to those having ordinary skill in the art and will vary in accordance with the cell targeted to receive the polynucleic acid. See, e.g., Sambrook et al., *Molecular Cloning: A Laboratory Manual,* Second Edition, Cold Spring Harbor (1989). Exemplary constructs include plasmids, phage vectors, and the like. For example, a polynucleic acid sequence containing about 1.6 kb, which encodes products that are produced at elevated levels in mammals having a predisposition to autoimmune disease, as compared to production levels of the same encoded products in normal mammals, was inserted into *E. coli* plasmid vector PCRII™ provided in the TA Cloning Kit™ (Invitrogen, San Diego, Calif.) using reagents provided in the kit according to the manufacturer's instructions. The resulting construct, identified as "pDHT-NOD1" was deposited with the American Type Culture Collection on Mar. 14, 1996, and assigned ATCC Accession No. 97479.

Introduction of the above-described constructs into appropriate host cells enables expression of the cloned polynucleic acid sequence. Appropriate expression vehicles are well known to those having ordinary skill in the art and include those that are replicable in eukaryotic cells and/or prokaryotic cells and those that remain episomal or those which integrate into the host genome. See, e.g., Sambrook et al., *Molecular Cloning: A Laboratory Manual*, Second Edition, Cold Spring Harbor (1989). Presently preferred vehicles for expression of the invention polynucleic acid sequences in eukaryotic host cells, particularly mammalian cells, include Rexp (with an RSV LTR, Moloney murine leukemia virus LTR driven expression vector), and the like. Presently preferred vehicles for expression of the invention polynucleic acid sequences in prokaryotic host cells, include *Escherichia coli, Bacillus subtilis*, yeast, and the like.

As used herein, a promoter region refers to a segment of polynucleic acid that controls transcription of DNA to which it is operatively linked. The promoter region includes specific sequences that are sufficient for RNA polymerase recognition, as well as binding and transcription initiation. This portion of the promoter region includes sequences that modulate the recognition, binding and transcription initiation activity of RNA polymerase. Promoters, depending upon the nature of the regulation, may be constitutive or inducible. For example, promoters contemplated for use in the practice of the present invention include the SV40 early promoter, the cytomegalovirus (CMV) promoter, Moloney murine leukemia virus (MMLV) promoter, thymidine kinase promoter, albumin promoter, Rous Sarcoma virus promoter (RSV), and the like.

As used herein, the term "operatively linked" refers to the functional relationship of polynucleic acid sequences with regulatory and effector sequences of nucleotides, such as promoters, enhancers, transcriptional and translational stop sites, and other signal sequences. For example, operative linkage of DNA to a promoter refers to the physical and functional relationship between invention DNA and the promoter, such that transcription of such DNA is initiated from the promoter by an RNA polymerase that specifically recognizes, binds to and transcribes the DNA.

In accordance with another embodiment of the present invention, there are provided host cells containing the above-described construct. Such host cells as bacterial, yeast and mammalian cells can be used for replicating polynucleic acids of the present invention and producing the same, or substantially the same polypeptides as set forth in SEQ ID NO 7, the same, or substantially the same polypeptides as are encoded by the polynucleotides set forth in SEQ ID NO 6, or the same, or substantially the same polypeptides as are produced by cultured cells containing the plasmid pDHT-NOD1 (identified by ATCC Accession No. 97479), under suitable expression conditions. Methods and conditions suitable to promote expression are well known in the art (see, e.g., Sambrook et al., *Molecular Cloning: A Laboratory Manual*, Second Edition, Cold Spring Harbor (1989)). Heterologous DNA may be introduced into host cells by any of a variety of methods known by those having ordinary skill in the art, such as, for example, transfection with a vector encoding the heterologous DNA by $CaPO_4$ precipitation. See, e.g., Kashanchi, F., et al., *Nucleic Acids Research*, 20:4673–4674 (1992).

In yet another embodiment of the present invention, there are provided polypeptides which are expressed at elevated levels in mammals having a predisposition to autoimmune disease. Polypeptides contemplated herein include those having the same, or substantially the same amino acid sequence as set forth in SEQ ID NO 7, polypeptides having the same, or substantially the same amino acid sequences as encoded by the polynucleic acid sequence set forth in SEQ ID NO 6, or polypeptides having the same, or substantially the same amino acid sequence as the polypeptides produced by cultured cells containing plasmid pDHTNOD1 identified by ATCC Accession No. 97479. As used herein, the terms "protein," "peptide," "polypeptide" and "amino acid sequence" are considered to be equivalent terms and are used interchangeably.

The invention further includes antibodies that are capable of binding to invention polypeptides, or fragments thereof. Such antibodies have utility in the diagnosis, prevention and treatment of autoimmune disease. In this context, the term "antibody" encompasses monoclonal antibodies, polyclonal antibodies and humanized antibodies. For example, for therapeutic applications, the antibodies employed will preferably be humanized.

The above-described antibodies can be prepared employing standard techniques, as are well known to those having ordinary skill in the art, using invention polypeptides or fragments thereof, as antigens for antibody production. Polyclonal antibodies of the present invention are typically produced by immunizing a mammal with an inoculum containing invention polypeptides, or fragments thereof, thereby inducing in the mammal, antibody molecules having immunospecificity for the above-described polypeptides and fragments thereof. Monoclonal antibody production typically proceeds by isolating lymphocytes and fusing them with myeloma cells, thus producing hybridomas. The cloned hybridomas are then screened for production of antibodies specific for invention polypeptides, or fragments thereof. Methods and conditions suitable for producing polyclonal and monoclonal antibodies are well known in the art (see, e.g., Harlow, et al., *Antibodies: A Laboratory Manual*, Cold Spring Harbor (1988)).

To enhance the specificity of the antibody, the antibodies can be purified, for example, by immunoaffinity chromatography using solid phase-affixed immunizing polypeptide. Thus, purification is achieved by contacting antibody with the solid phase-affixed immunizing polypeptide for a time sufficient for the polypeptide to immunoreact with antibody to form a solid phase-affixed immunocomplex. Bound antibodies are then separated from the complex by standard techniques.

The antibody so produced can be used in diagnostic and assay methods to detect the quantities of invention polypeptides expressed by a subject. Expression at higher levels, as compared to expression of the same polypeptides in normal mammals, is indicative of autoimmune disease predisposition. Thus, in accordance with another aspect of the invention, methods of screening for predisposition to autoimmune disease are provided. Such methods comprise:

a) contacting a biological sample with antibody that selectively binds polypeptide expressed at elevated levels in mammals having a predisposition to autoimmune disease, under conditions suitable for the formation of a first complex between the antibody and polypeptide;

b) determining the quantity of the first antibody-polypeptide complex;

c) contacting a control sample with the antibody under conditions suitable to form a second antibody-polypeptide complex;

d) detecting the quantity of second complex; and e) comparing the quantities of first and second complexes.

As used herein, the term "control sample" refers to a biological sample obtained from a mammal that is not predisposed to autoimmune disease. The determination of whether a mammal is predisposed to autoimmune disease is made on the basis of clinical diagnosis for the particular autoimmune disease by a physician or veterinarian having ordinary skill in the art. As contemplated herein, a mammal is normal (i.e., not predisposed to autoimmune disease) if it is completely free of clinical symptoms of the particular autoimmune disease.

Optionally, steps (c)–(e) can be omitted by determining, in normal mammals, the baseline or average quantity of invention polypeptide in a biological sample. This can readily be done by carrying out steps (c) and (d) on a number of normal mammals from a given species and determining the average quantity of invention polypeptide detected, thereby establishing a standardized normal quantity of invention polypeptide or normal level of expression of invention polypeptide. This standardized value can be used for comparison purposes to determine whether a particular biological test sample is positive or negative for autoimmune disease predisposition.

Biological samples employed in the practice of the present invention, include, for example, pancreatic tissue (e.g., islet cells), splenocytes, peripheral blood leukocytes, and the like.

As contemplated in the practice of the present invention, a mammal is identified as being predisposed to autoimmune disease if the ratio of the quantity of the first complex to the quantity of the second complex (or the ratio of the quantity of the first complex to the standardized normal quantity of expression product), is at least about two. Preferably, a positive determination of predisposition to autoimmune disease is made when the above-described ratio is at least about three. Most preferably, a positive determination of predisposition to autoimmune disease is made when the above-described ratio is at least about four.

In accordance with another embodiment of the present invention, there are provided methods for screening for autoimmune disease predisposition based on detection of the quantity of mRNA encoded by polynucleic sequences of the present invention. These methods comprise:

a) contacting a biological sample with oligonucleotide probes that are substantially complementary to portions of mRNA associated with polynucleic acids of the present invention, under conditions suitable for hybridization to occur between the probe and the mRNA to form a first hybridized complex;

b) determining the quantity of first hybridized complex;

c) contacting a control sample with the oligonucleotide probe, under conditions such that a second complex is formed between the probe and mRNA associated with invention polynucleic acid sequences in the control sample;

d) determining the quantity of second complex; and e) comparing the quantity of first complex to the quantity of second complex.

Optionally, steps (c)–(e) can be omitted by determining, in normal mammals the baseline or average quantity of invention mRNA in a biological sample. This can be done by carrying out steps (c) and (d) on a number of normal mammals from a given species and determining the average quantity of invention mRNA detected, thereby establishing a standardized normal quantity of invention mRNA or normal level of transcription of invention mRNA. This standardized value can then be used for comparison purposes to determine whether a particular biological sample is positive or negative for autoimmune disease predisposition.

As contemplated in the practice of the present invention, a mammal is deemed to be predisposed to autoimmune disease if the ratio of the quantity of the first probe-mRNA complex to the quantity of the second, control probe-mRNA complex (or the ratio of the quantity of the first probe-mRNA complex to the standardized normal quantity of invention mRNA in a biological sample), is at least about two. Preferably, a positive determination of predisposition to autoimmune disease is made when the above-described ratio is at least about three. Most preferably, a positive determination of predisposition to autoimmune disease is made when the above-described ratio is at least about four.

Preferably, antibodies and oligonucleotide probes of the present invention are detectably labeled to facilitate identification of the presence of antibody-polypeptide and probe-mRNA complexes. A description of labeling techniques for oligonucleotide probes is described above. Antibodies can be labeled with a variety of detectable compounds. For example, the detectable label can be a fluorescent labeling agent that chemically binds to antibodies without denaturing them to form a fluorochrome (dye) useful as an immunofluorescent tracer. Suitable fluorescent labeling agents are fluorochromes such as fluorescein isocyanate (FIC), fluorescein isothiocyanate (FITC), 5-dimethylamino-1-naphthalenesulfonyl chloride (DANSC), tetramethylrhodamine isothiocyanate (TRITC), lissamine, rhodamine 8200 sulphonyl chloride, and the like. A description of immunofluorescence analysis techniques is found in DeLuca, "Immunofluorescence Analysis", in *Antibody as a Tool*, Marchalonis et al., eds., John Wiley & Sons, Ltd., pp. 189–231 (1982), which is incorporated herein by reference.

Radioactive elements are also useful detectable labels for antibodies. An exemplary radiolabeling agent is a radioactive element that produces gamma ray emissions. Elements which themselves emit gamma rays, such as $^{125}$I and $^{131}$I, represent one suitable class of gamma ray emission-producing radioactive element indicating groups.

In one embodiment of a labeled antibody, the detectable label is an enzyme, such as horseradish peroxidase (HRP), glucose oxidase, and the like. In such cases where the detectable marker is an enzyme (such as HRP or glucose oxidase), additional reagents are typically required to indicate that the antibody-polypeptide complex has formed. Such additional reagents for HRP include hydrogen peroxide and an oxidation dye precursor such as diaminobenzidine, o-phenylenediamine dihydrochloride, and the like. An additional reagent useful with glucose oxidase is 2,2'-azino-di-(3-ethyl-benzthiazoline-G-sulfonic acid).

Depending on the nature of the label or catalytic signal producing system used, a signal can be detected by: (1) irradiating the complexed test sample with light and observing the level of fluorescence; (2) contacting the complexed sample with a substrate which can be catalytically converted by the label to produce a dye, fluorescence or chemiluminescence, in which the formation of dye can be observed visually or in a spectrophotometer; or (3) employing a radiation counter such as a gamma counter to detect gamma emitting labels such as $^{125}$I. For detection of enzyme-catalyzed labels when the presently preferred combination of HRP is used as the enzyme and o-phenylenediamine dihydrochloride as the substrate, a quantitative analysis of complex can be made using a spectrophotometer (e.g., a EMAX Microplate Reader available from Molecular Devices, Menlo Park, Calif.) at 405 nm in accordance with the manufacturer's instructions.

One method for detecting the presence of antibody-bound complex employs an "ELISA" format that provides for the detection and quantification of either antibody or antigen (depending on the ELISA format type) present in a sample. ELISA is a well-known technique that can be readily carried out by those having ordinary skill in the art. A description of the ELISA technique is found in Chapter 22 of the 4th Edition of *Basic and Clinical Immunology*, by D.P. Sites et al., published by Lange Medical Publications of Los Altos, Calif. in 1982, incorporated herein by reference. ELISA formats employed in the practice of the present invention include formats based on invention antibody, or antigen derived from invention polynucleic acids, encoded products thereof, or fragments thereof, that are bound to a solid matrix.

Useful solid matrices are well known in the art. Such materials are water insoluble and include crosslinked dextran (available from Pharmacia Fine Chemicals; Piscataway, N.J.), agarose, polystyrene beads (typically about 1 micron to about 5 millimeters in diameter, available from Abbott Laboratories, Chicago, Ill.), polyvinyl chloride, polystyrene, crosslinked polyacrylamide, nitrocellulose- or nylon-based webs such as sheets, strips or paddles, or tubes, plates or the wells of a microtiter plate, such as those made from polystyrene or polyvinylchloride, and the like.

In accordance with another embodiment of the present invention there are provided antisense oligonucleotides and DNA sequences encoding antisense oligonucleotides. As contemplated in the practice of the present invention, antisense oligonucleotides and DNA sequences encoding antisense oligonucleotides can be readily prepared that bind to and therefore block the synthesis of invention mRNA encoding invention polypeptides. Thus, these compounds can be administered to subjects to inhibit the development of autoimmune disease. One of ordinary skill in the art will appreciate that when formulations of the present invention (e.g., antibodies, antisense oligonucleotides, or DNA sequences encoding antisense oligonucleotides) are administered as therapeutic agents, it may be necessary to combine these compositions with other suitable components to form a suitable pharmaceutical formulation. The particular formulation will depend on the intended use and mode of administration.

The present invention contemplates pharmaceutical formulations useful for practicing the therapeutic methods described herein. Pharmaceutical formulations of the present invention may contain a physiologically acceptable carrier together with antisense oligonucleotides, DNA encoding antisense oligonucleotides, or antibodies, as described herein, dissolved or dispersed therein as an active ingredient. In a preferred embodiment, the pharmaceutical formulation is not immunogenic when administered to a mammal or human patient for therapeutic purposes. This may be accomplished, for example, by using commonly known techniques of "humanizing" antibodies wherein the constant regions of an antibody derived from a non-human animal are replaced with constant regions derived from a human antibody.

As used herein, the term "pharmaceutically acceptable" and grammatical variations thereof, as they refer to compositions, formulations, carriers, diluents and reagents, are used to represent that the materials are capable of administration to a mammal without the production of undesirable physiological effects such as nausea, dizziness, gastric upset, and the like.

The preparation of a pharmaceutical formulation that contains active ingredients dissolved or dispersed therein is well known in the art. Typically such formulations are prepared as tablets, capsules, or injectables, either as liquid solutions or suspensions. However, solid forms suitable for incorporation into a liquid as a solution or suspension prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol, and the like, as well as combinations of any two or more thereof.

The therapeutic formulation of the present invention can include pharmaceutically acceptable salts of the components therein. Pharmaceutically acceptable nontoxic salts include acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like, as well as combinations of any two or more thereof.

Salts formed with the free carboxyl groups of amino acid sequences of the present invention can also be derived from inorganic bases, such as, for example, sodium hydroxide, ammonium hydroxide, potassium hydroxide, and the like; organic bases such as mono-, di-, and tri-alkyl and -aryl amines (e.g., triethylamine, diisopropyl amine, methyl amine, dimethyl amine, and the like), ethanolamines (e.g., ethanolamine, diethanolamine, and the like), and the like, as well as combinations of any two or more thereof.

Physiologically acceptable carriers are well known in the art. Exemplary liquid carriers are sterile aqueous solutions that contain the active ingredients and water or a buffer, such as, for example, sodium phosphate buffer at physiological pH, physiological saline or both, such as phosphate-buffered saline, and the like. Still further, aqueous carriers can contain more than one buffer salt, as well as salts, such as sodium and potassium chlorides, dextrose, polyethylene glycol and other solutes, and the like.

Liquid compositions can also contain liquid phases in addition to (or to the exclusion of) water. Examples of such additional liquid phases are glycerin, vegetable oils such as cottonseed oil, water-oil emulsions, and the like.

A therapeutically effective amount of antisense oligonucleotides, DNA encoding antisense oligonucleotides, or antibodies of the present invention is a predetermined amount calculated to achieve the desired effect, e.g., inhibition of the development of autoimmune disease. The required dosage for inhibiting autoimmune disease will depend on a variety of factors, including the age, weight, sex and medical condition of the patient, as well as the severity of the pathology, the route of administration, the type of therapeutic agent used, and so on. A skilled physician or veterinarian can readily determine and prescribe the effective amount of the pharmaceutical formulation required to treat the patient. Conventionally, one of ordinary skill in the art would employ relatively low doses initially and subsequently increase the dose until a maximum response is obtained.

Kits for use in screening for predisposition to autoimmune disease are also provided by the present invention. Such kits include some or all of the reagent primers, probes, antibodies, and control samples described herein for determining the quantities of mRNA, peptides, polypeptides, and proteins, encoded by polynucleic acids of the present invention, or fragments thereof. Kits of the present invention may contain, for example, restriction endonuclease, one or more labeled cDNA probes, lyophilized antibody that is capable of binding to encoded products associated with invention polynucleic acid sequences or fragments thereof, lyophilized secondary antibodies that are conjugated to a fluorochrome or peroxidase (in combination with an appropriate amount of hydrogen peroxide substrate) and that are capable of binding invention antibodies, blocking solutions (e.g., normal goat or rabbit serum, 3% bovine serum albumin solution in physiological saline, and the like), buffers (e.g., Tris-HCl, phosphate, EDTA, and the like), and the like, or combinations of any two or more thereof.

The invention will now be described in greater detail by reference to the following non-limiting examples.

EXAMPLE 1

Isolation of mRNA from Female NOD Mice

Several features of the genetics and immunopathology of diabetes in the Non-Obese Diabetic (NOD) mouse are also shared with human diabetes. These features include autoantibodies to islet beta cells, defects in T-cell function and the association of the disease with major histocompatibility complex (MHC) genes. Castano, L., et al. *Annu. Rev. Immunol.*, 8:647 (1990). In NOD mice, insulitis (islet inflammation), a prerequisite stage to developing diabetes, begins at 4–5 weeks of age and is present in 100% of females and more than 90% of males at 30 weeks of age. Kikutani, H., et al. *Adv. Immunol.*, 51:285–322 (1992). Onset of insulin-dependent diabetes mellitus typically begins at 8–10 weeks of age and is more frequently observed in females with an incidence reaching 65% by the age of 36 weeks compared to males, in whom the incidence stays below 5%, even at 30 weeks of age.

Using the guanidium thiocyanate method described by Chomczynski and Sacchi, *Anal. Biochem.*, 162:156–157 (1987), mRNA was extracted from the splenocytes of two groups of female NOD mice: 1) 3 to 5 week old, nondiabetic (i.e., prior to onset of insultis); and 2) 14 to 16 week old, prediabetic (i.e., after onset of advanced insulitis). Specifically, splenocytes from the female NOD mice were placed into test tubes. A 0.5 ml aliquot of a solution of 4M guanidine thiocyanate, 25 mM sodium citrate (pH 7.0), 0.5% N-lauroylsarcosine, and 0.1M 2-mercaptoethanol was added to the tissue sample in each test tube. The test tubes were agitated for up to 24 hours at room temperature. The following aliquots were added to each tube: 1) 0.1 ml of a chloroform/isoamyl alcohol 24:1 v/v solution; 2) 0.5 ml of phenol (free acid form); and 3) 50 µl of 3M sodium acetate.

The tubes were then centrifuged at a centrifugation rate of 12,000×g for 20 minutes to pellet the splenocytes. The aqueous phase from each tube was transferred by pipet into a clean tube. An aliquot of 1.5 ml of ethanol was added to the aqueous phase in each tube to precipitate the RNA. The tubes were allowed to stand on a test tube rack at −80° C. for 2 hours, then centrifuged again at a centrifugation rate of 12,000×g for 20 minutes to generate an RNA pellet.

The pellets were each washed with a 1 ml aliquot of 75% ethanol. After washing, the pellets were air-dried at room temperature for 5 minutes. The pellets were then resuspended in 10–20 µl digestion buffer (10 mM Tris-HCl and 2 mM ethylene diamine tetraacetic acid (EDTA)), then treated with 20 units (u) of DNase-free RNase (Sigma Chemical Co., St. Louis, Mo.) for 30 minutes at 37° C. To remove the DNase-free RNase, the phenol/chloroform extraction procedure was repeated a second time on the pellet, immediately followed by ethanol precipitation, as described above. After the precipitation step, the pellets were washed in distilled water.

The optical density of RNA in distilled water was measured at wavelengths of 260 nm and 280 nm using a Beckman, DU 640 Spectrophotometer (U.S.A.). The $OD_{260}/OD_{280}$ ratio was used to quantitate the amount of RNA extracted and also to determine the purity of each preparation.

EXAMPLE 2

Isolation of a Polynucleic Acid Sequence that is Functionally Associated with Development of IDDM Reverse transcription of 100 ng of mRNA isolated from the 3 to 5 week old, nondiabetic (i.e., insulitis-free) and the 14 to 16 week old, prediabetic (i.e., with advanced insulitis) female NOD mice from Example 1 was conducted at 36° C. using the GeneAmp® RNA PCR Kit (Perkin-Elmer-Cetus, Norwalk, Conn.) according to the manufacturer's directions. Amplification of the resulting cDNA was carried out by using the GeneAmp® PCR Kit according to the manufacturer's directions.

Primers used for reverse transcription and PCR amplification of the reverse transcribed cDNA are set forth in SEQ ID NO 2 (upstream primer) and SEQ ID NO 3 (downstream primer). The GeneAmp® PCR System 9600 (Perkin-Elmer-Cetus, Norwalk, Conn.) thermal cycler was used to control the PCR reactions. Programmable temperature cycling was performed with the following cycle profile: 94° C. for 1 minute, then 35 cycles of each of the following:

1) denaturation for 30 seconds at 94° C.;

2) annealing for 1 minute at 420° C.;

3) 72° C. for 30 seconds; and 4) elongation for 5 minutes at 72° C.

After 35 cycles, the reaction tubes were incubated at 72° C. for 5 minutes, then cooled to 4° C.

The amplified cDNA sequences were displayed on a 6% denaturing PAGE (6M urea) gel using the Pokerface™ SE 1500 sequencing apparatus (Hoefer Scientific Instrument, San Francisco, Calif.), according to the manufacturer's instructions. Samples were also electrophoresed on a 6% non-denaturing PAGE gel. The gels were autoradiographed using Kodak XAR-5 film (Rochester, N.Y.). Examination of the autoradiographed gel patterns of amplified cDNA sequences revealed a difference in signal intensity of a particular cDNA fragment that was common to both 3 to 5 week old NOD splenocyte samples and 14 to 16 week old NOD splenocyte samples. The signal intensity of this particular cDNA fragment appeared greater in the autoradiograph associated with the 14 to 16 week old NOD splenocyte samples as compared to the autoradiograph associated with the 3 to 5 week old NOD splenocyte samples.

These results indicate that mRNA associated with the isolated cDNA fragment is transcribed at a greater level in 14 to 16 week old (with advanced insulitis) female NOD mice, as compared to 3 to 5 week old (insulitis-free) female NOD mice.

EXAMPLE 3

Sequencing of the Isolated cDNA

Sequencing of the isolated cDNA from Example 2 was conducted according to the Sanger method of sequencing.

Bands were cut from the gel used in Example 2 and sequenced using the Fmol DNA Sequencing System (Promega, Madison, Wis.) containing Taq polymerase (United States Biochemical, Cleveland, Ohio) and ($^{32}$P) dCTP (Amersham, Arlington Heights, Ill.) according to the manufacturer's directions. Plasmid template cDNA was prepared for sequencing according to the commercial protocol provided by Promega Biotec (Madison, Wis.). The gels were photographed onto Kodak Diagnostic Film SB 100 (Rochester, N.Y.). The Pokerface™ SE 1500 sequencing apparatus (Hoefer Scientific Instrument, San Francisco, Calif.) was used to sequence the gels.

The 358 bp polynucleic acid set forth in Seq ID NO 1 was sequenced and compared with known sequences in Genbank. No known sequence matched this sequence.

EXAMPLE 4

Preparation of a cDNA Probe for Detecting mRNA Encoded by DNA that is Functionally Associated with IDDM Development Primers were designed to amplify a cDNA probe complementary to cellular mRNA associated with the polynucleotide sequence set forth in SEQ ID NO 1. The primers identified as SEQ ID NO 4 (upstream primer) and SEQ ID NO 5 (downstream primer) were used in the polymerase chain reaction method described above in Example 2.

A search in Genbank indicated that these primers would not hybridize to any other known nucleic acid sequences under the conditions used.

The isolated cDNA probe was characterized by electrophoresis on a 6% PAGE gel as described in Example 2, then sequenced according to the method described in Example 3. The amplified cDNA probe was 189 base pairs long. The sequence of this novel probe is the sequence extending from base pair number 73 to base pair number 261 of SEQ ID NO 1. A search was conducted to compare the 189 bp sequence to known sequences in Genbank. No gene matched this sequence.

EXAMPLE 5

Confirmation of the Functional Association Between the Polynucleic Acid Isolated in Example 2 and IDDM Development To confirm the association between the cDNA isolated in Example 2 and insulin-dependent diabetes mellitus, quantities of mRNA associated therewith were evaluated in cells treated with agents that inhibit IDDM onset in pre-diabetic cells, as described below.

I. Effect of 5-Dihydrotesterone (5-DHT) on Development of Insulin-Dependent Diabetes Mellitus Seven female NOD mice, age 3 to 5 weeks, were given pellets of 5-DHT by subcutaneous implantation using a 10 gauge trochar (Innovative Research of America, Toledo, Ohio). The 5-DHT pellets were designed by Innovative Research of America (Toledo, Ohio) to deliver 15 mg of 5-DHT over 60 days, yielding plasma 5-DHT levels of 5–10 ng/ml (17–34 nM). Eight control mice were implanted with pellets containing the carrier-binder alone. After 60 days, all mice received a second implantation of 5-DHT or placebo pellets, as appropriate.

After an additional 60 days, 3 NOD mice each from the treated and control groups were sacrificed. Pancreata from the sacrificed NOD mice were subjected to histological analyses using hematoxylin-eosin staining fixed in Bouin's solution as described by Toyoda, et al. in *Immunol. Lett.*, 32:241–246 (1992). Islet mononuclear cell infiltration and islet beta-cell destruction were graded. The 5-DHT-treated mice showed typical histologically normal islet structure with no signs of periductal or pervascular infiltrates. In contrast, islet cells from control group pancreata revealed severe peri-insulitis, with some structures completely degranulated.

By 37 weeks of age, none of the remaining 5-DHT-treated mice had developed diabetes. In contrast all remaining mice that received placebo pellets developed diabetes. All treated mice survived without developing the disease for almost one year after stopping the administration at 120 days. Hence, administration of 5-DHT for 120 days at an age prior to the onset of insulitis inhibited the development of IDDM in NOD mice.

II. Effect of 5-DHT on Expression of a Gene Associated with Isolated cDNA from Example 2

Four female NOD mice, age 3 to 5 weeks were given pellets that delivered 15 mg of 5-DHT over 60 days by subcutaneous implantation, which yielded plasma 5-DHT levels of 5–10 ng/ml (17–34 nM), as described above (i.e., the "treated group"). A group of untreated, female NOD mice received pellets containing the carrier-binder alone. Using the guanidine-thiocyanate method described in Example 2, mRNA was extracted from the splenocytes of untreated pre-diabetic NOD mice with advanced insulitis (14–16 weeks old), age-matched 5-DHT-treated NOD mice, and insultis-free (3–5 weeks old) female NOD mice. Messenger RNA (100 ng) from each experimental group was subjected to RT-PCR, as described in Example 2 using primers identified as SEQ ID NO 4 (upstream primer) and SEQ ID NO 5 (downstream primer). The product was electrophoresed on a 6% PAGE gel and stained with ethidium bromide.

Densitometry was used to characterize the quantities of cDNA according to the method described by Toyoda, et al., *Immunol. Lett.*, 32:241–246 (1992). Results from a densitometric analysis are shown in FIG. 1. Results are plotted as the ratio of optical density of cDNA associated with invention mRNA to optical density of cDNA associated with β-actin gene. The quantity of cDNA associated with invention mRNA was normalized against β-actin gene expression, which is believed to be unaffected by 5-DHT, PHA, and Con A stimulation. β-actin gene product was amplified by RT-PCR using mouse β-actin primers set forth in SEQ ID NO 9 (upstream primer) and SEQ ID NO 10 (downstream primer). The amplified cDNA product of β-actin gene using these primers was 551 bp in length.

The results indicate that quantities of invention mRNA were elevated in the untreated, 14 to 16 week old, diabetic mice to a level of about three times the quantity of invention mRNA in the 3 to 5 week old non-diabetic mice, and the age-matched 5-DHT-treated, diabetic mice. Accordingly, the development of insulin-dependent diabetes mellitus correlates with elevated levels of mRNA of the present invention.

Accordingly, the inhibitory effect of 5-DHT on IDDM development in female NOD mice confirms the relationship between elevated levels of mRNA of the present invention and development of insulin-dependent diabetes mellitus.

III. Effect of Concanavalin A on Expression of DNA Associated with Isolated cDNA from Example 2

Administration of concanavalin A (Con A) to prediabetic NOD mice has been shown to prevent the development of diabetes by activating suppressor T-cells that suppress the expansion of autoreactive T cells. Pearce, R. B., et al., "Studies of concanavalin A in nonobese diabetic mice. I.

Prevention of insulin-dependent diabetes," *J. Pharmacol. Exp. Ther.*, 258:710–715 (1991).

Splenocytes (1×10⁶/ml) from non-diabetic NOD female mice with no insulitis (3–5 weeks old) and prediabetic mice with advanced insulitis (14–16 weeks old) were stimulated with Con A (4 μg/ml) overnight, followed by RT-PCR, as described in Example 2. Quantitation of invention cDNA levels was conducted as described in part II above.

Figure 2:
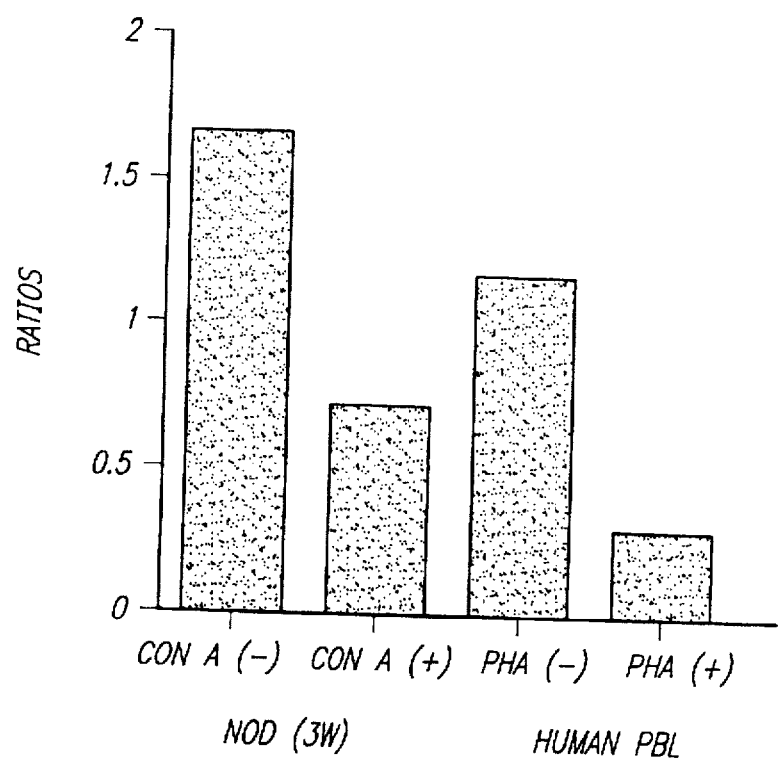
FIG. 2 illustrates the differential quantities of cDNA of the present invention associated with mRNA obtained from: (1) splenocytes from untreated, 3 to 5 week old, female non-diabetic (i.e., prior to onset of insulitis) NOD mice; (2) splenocytes from concanavalin A(ConA)-treated, 3 to 5 week old female NOD mice; and (3) phytohemagglutinin (PHA)-treated human peripheral blood leukocytes from normal non-diabetic individuals. For each splenocyte sample, the quantity of cDNA associated with mRNA transcribed from polynucleic acid of the present invention (i.e., invention cDNA) is expressed as a ratio of the optical density of invention cDNA to the optical density of cDNA associated with mRNA transcribed from control gene, α-actin gene, in the same sample.

Results from the densitometric analysis are shown in FIG. 2. The results indicate that the quantity of cDNA associated with invention mRNA in untreated NOD mice was more than five times higher than the quantity of the same cDNA in Con A-treated splenocytes. These results, coupled with the reported effect of Con A on suppression of autoreactive T cells, are consistent with polynucleic acid of the present invention being functionally related to autoimmune disease in general.

IV. Effect of Phytohemagglutinin on Transcription of the Isolated Gene in Human Peripheral Blood Leukocytes Phytohemagglutinin (PHA) is a glycoprotein derived from red kidney beans. PHA is known to induce T cell activation in peripheral blood leukocytes (PBL). See, e.g., *Immunochemistry*, van Oss, et al., eds., Marcel Dekker, Inc., pp. 310–11 (1994). Human peripheral blood leukocytes (PBL) (1×10⁶ cells/ml) from a health normal individual were stimulated with 5 μg/ml PHA (Sigma Chemical Co., St. Louis, Mo.), followed by RT-PCR, electrophoresis, and densitometric analysis, as described above.

Results from the densitometric analysis are shown in FIG. 2. The results indicate that the quantity of cDNA associated with invention mRNA in untreated NOD mice was more than five times higher than the quantity of the same cDNA in PHA-treated PBL. These results, coupled with the reported effect of PHA on suppressor T cell activation, are consistent with polynucleic acid of the present invention being functionally related to autoimmune disease in general.

EXAMPLE 6
Isolation of Full cDNA Clone of Gene that is Functionally Associated with Autoimmune Disease A cDNA library was prepared by RT-PCR using the mouse spleen mRNA and primers provided in the Marathon-Ready cDNA kit (Clontech, Palo Alto, Calif.) according to the manufacturer's directions. The amplified cDNA sequences were electrophoresed on a 6% PAGE gel and transferred to a nylon membrane (Schleicher & Schull, Keene, N.H.). The nylon filter was probed with a $^{32}$P-labeled probe having the sequence extending from base pair number 73 to base pair number 261 of SEQ ID NO 1 (i.e., the 189 bp probe described in Example 4).

Comparison with molecular weight markers indicated that the isolated cDNA was 1.6 kb long. The cDNA was sequenced according to the method described in Example 3. Partial sequences of this cDNA are set forth in SEQ ID NO 6 and SEQ ID NO 8.

SEQ ID NO 6 encodes what is believed to be a carboxy-terminal amino acid sequence extending from base pair number 1 to base pair number 27, followed by a 3' untranslated sequence containing 352 nucleic acid residues. The amino acid sequence encoded by the sequence extending from base pair number 1 to base pair number 27 of SEQ ID NO 6 is set forth in SEQ ID NO 7.

SEQ ID NO 8 contains a partial sequence of the 5' end of the isolated 1.6 kb clone and contains 461 nucleic acid residues.

A search in Genbank indicated that SEQ ID NO 6 and SEQ ID NO 8 are unique. The 1.6 kb isolated clone was inserted into *E. coli* plasmid vector PCRII™ provided in the TA Cloning Kit™ (Invitrogen, San Diego, Calif.) using reagents provided in the kit according to the manufacturer's instructions. The resulting construct, identified as "pDHT-NOD1" was deposited on Mar. 14, 1996 with the American Type Culture Collection, 12301 Parklawn Drive, Rockville, Md. 20852, and assigned ATCC Accession No. 97479.

EXAMPLE 7
Method of Screening Various Types of Tissue for Predisposition to Autoimmune Disease Messenger RNA is extracted from peripheral blood leukocytes (PBL) from a test subject by the guanidium thiocyanate method described in Example 2. The extracted mRNA is subjected to RT-PCR using the GeneAmp® PCR kit (Perkin-Elmer-Cetus, Norwalk, Conn.) and the primers identified as SEQ ID NO 4 and SEQ ID NO 5 (as described in Example 4) to determine the copy number of mRNA that is functionally associated with autoimmune disease predisposition.

RT-PCR, as described above, is also performed on mRNA extracted from a PBL sample taken from a normal (control) subject (i.e., a subject known not to be afflicted with autoimmune disease, based on a clinical diagnosis). The ratio of copy number of invention mRNA derived from the test subject to copy of invention mRNA derived from the control subject is calculated to determine whether the test subject is predisposed to developing autoimmune disease. A ratio of at least about two is indicative of autoimmune disease predisposition.

Alternatively, mRNA extracted from the test subject and control subject is resolved on a 1.5% agarose-formaldehyde gel by applying 18 mAMPs for 16 hours. The extracted mRNA is then transferred to a nylon membrane (Schleicher & Schull, Keene, N.H.) by capillary action. The transferred mRNA is fixed onto the membrane by exposing the mRNA-containing nylon membrane to short-wave ultraviolet radiation in a Stratalinker (Stratagene, La Jolla, Calif.) for 40 seconds according to the manufacturer's directions.

The membranes are pre-hybridized for 1 hour at 640° C. with a solution of 50% deionized formamide, 7% sodium dodecyl sulfate (SDS), 10% bovine serum albumin (Sigma, St. Louis, Mo.), 1 mM EDTA and 0.2M sodium phosphate (pH 7.2). The 189 bp cDNA probe for the novel DNA, described in Example 4, or alternatively, the 358 bp CDNA probe identified in SEQ ID NO 1, is radiolabeled with $^{32}$P by random primer oligolabeling in the presence of dCT ($\alpha^{32}$P) . The nylon membranes are hybridized in the presence of the $^{32}$P-CDNA probes by adding the probes to the pre-hybridization solution for a hybridization period of 16 hours at 640° C. After hybridization, the membranes are briefly washed three times in a 20 ml/membrane solution of 40 mM sodium phosphate, 1 mM EDTA, and 1% SDS at 640° C. for three short washes, followed by a final 1 hour wash. The membranes are exposed to preflashed Kodak XAR-5 film (Rochester, N.Y.) at −700° C. for 2 to 14 days.

The ratio of signal associated with invention mRNA derived from the test subject to signal associated with invention mRNA derived from the control subject is calculated to determine whether the test subject is predisposed to developing autoimmune disease. A ratio of at least about two is indicative of autoimmune disease predisposition.

EXAMPLE 8
Preparation of Polyclonal Antibodies Raised Against a Polypeptide that is Functionally Related to Autoimmune Disease Peptides synthesized according to the sequence set forth in SEQ ID NO 7 are conjugated to keyhole limpet hemacyanin (KLH) and bovine serum albumin (BSA) according to the manufacturer's instructions (Imgect, Immunogen Conjugation Kit fro Pierce Chemical Co., Rockford, Ill.). Immunogen is prepared by mixing KLH-conjugated peptides thoroughly with Freund's complete adjuvant (Pierce Chemical Co., Rockford, Ill.) in a 1:1 v/v ratio. A dose of 100–200 µg of the immunogen is then injected subcutaneously in 10 sites in 3 young New Zealand White rabbits per peptide. Just prior to immunization, 5–10 ml of preimmune blood is collected through the ear vein. On days 14 and 28, the rabbits are boosted by the same injection route using immunogen in incomplete Freund's adjuvant. Starting from day 28, blood is collected twice a week (up to 30 ml each time) for up to 3 months and assayed by standard peroxidase/DAB-based ELISA (kit from Pierce) against BSA-conjugated peptide, with preimmune serum as a negative control. Sera from positive bleeds are pooled and IgG is isolated by protein A-agarose (Sigma, St. Louis, Mo.) affinity chromatography. Immune IgG is further purified by affinity chromatography on columns with peptide immobilized on agarose beads. Purified IgG is tested for reaction by immunoprecipitation, Western blotting and immunohistochemistry.

EXAMPLE 9

Preparation of Monoclonal Antibody Having Binding Specificity to a Polypeptide that is Functionally Associated with the Development of Autoimmune Disease Peptides synthesized according to the sequence set forth in SEQ ID NO 7 are conjugated to keyhole limpet hemocyanin (KLH) and bovine serum albumin (BSA) according to the manufacturer's instructions (Imgect, Immunogen Conjugation Kit from Pierce Chemical Co., Rockford, Ill.). One month old Balb/c mice (10 mice per peptide) are bled through the tail vein on day one and immunized intraperitoneally using 20–100 µg KLH-peptide complex (day one, in complete Freund's adjuvant (Pierce Chemical Co., Rockford, Ill.); day 14, in incomplete Freund's adjuvant (Pierce Chemical Co., Rockford, Ill.); day 28, in incomplete Freund's adjuvant. On day 35, the injection is given intravenously without adjuvant. If only BSA-peptide complex is soluble, it is injected instead of the KLH-peptide complex. On day 38, the mice are sacrificed by cervical dislocation, the splenocytes removed, washed in cold Dulbecco's MEM (DMEM) without serum and fused with mouse myeloma X-63 Ag 8.563 at 37° C. for 1.5 minutes using polyethylene glycol (PEG), molecular weight 1,500 (Merck, N.J.).

After washing out the PEG three times using DMEM with 10% bovine serum, cells are seeded in DMEM with 20% fetal bovine serum and HAT supplement on 96 well plates with preseeded feeder splenocytes from normal mice (one normal feeder spleen for 4 plates, and one immune spleen for 6 plates). The cultures are left for 7–10 days. Culture medium is changed once a week until clonal growth is observed. Positive hybridoma clones are assayed by indirect immunofluorescence on tissue sections and/or ELISA and propagated until enough antibody is collected. Positive hybridomas are frozen during subculture on a weekly basis.

Although the invention has been described with reference to presently preferred embodiments, it should be understood that various modifications can be made without departing from the spirit of the invention.

That which is claimed is:

1. An isolated polynucleic acid, comprising an oligonucleotide selected from the group consisting of SEQ ID NO 1, SEQ ID NO 6, and SEQ ID NO 8; and fragments at least 20 nucleotides long.

2. The polynucleic acid of claim 1, comprising SEQ ID NO 1, or fragments thereof at least 20 nucleotides long.

3. The polynucleic acid of claim 1, comprising SEQ ID NO 6, or fragments thereof at least 20 nucleotides long.

4. The polynucleic acid of claim 1, comprising SEQ ID NO 8, or fragments thereof at least 20 nucleotides long.

5. The polynucleic acid of claim 1, comprising a 1.6 kb DNA fragment carried by a plasmid having the ATCC Accession No. 97479, or fragments thereof at least 20 nucleotides long.

6. The polynucleic acid of claim 1, which is a DNA.

7. The polynucleic acid of claim 1, which is an RNA.

8. The polynucleic acid of claim 1, comprising an oligonucleotide selected from the group consisting of oligonucleotides encoding SEQ ID NO 7 and fragment thereof at least 20 contiguous nucleotides long.

9. The polynucleic acid of claim 1, being a fragment, wherein the fragment is at least 40 contiguous nucleotides long.

10. The polynucleic acid fragment of claim 9, which is at least 60 contiguous nucleotides long.

11. The polynucleic acid fragment of claim 10, which is at least 150 contiguous nucleotides long.

12. A construct, comprising
the polynucleic acid of claim 1;
an origin of replication; and
a promoter.

13. A vector, comprising the construct of claim 12.

14. The vector of claim 13, having the ATCC Accession No. 97479.

15. An anti-sense polynucleotide, complementary to the nucleic acid of claim 1.

16. The anti-sense polynucleotide of claim 15, which is a DNA.

17. The anti-sense polynucleotide of claim 15, which is an RNA.

18. A mRNA, corresponding to the polynucleic acid of claim 1.

19. A cDNA, complementary to the mRNA of claim 18.

20. The polynucleic acid of claim 8, wherein the oligonucleotide is selected from the group consisting of nucleotides 1 to 27 of SEQ ID NO 6, or fragments thereof.

21. A labeled polynucleic acid, comprising the polynucleic acid of claim 1, in labeled form.

22. The labeled polynucleic acid of claim 21, wherein the label is selected from the group consisting of $^{32}$P, $^{14}$C, $^{125}$I, $^{3}$H, $^{35}$S, biotin, fluorescent labels, enzymes, and other protein.

23. A polynucleotide, complementary to the polynucleic acid of claim 5.

24. A probe primer, complementary to the polynucleic acid of claim 8.

25. A vector, comprising the polynucleic acid of claim 1.

26. The polynucleic acid of claim 3, comprising nucleotides 1to 27 of SEQ ID NO 6.

27. A composition, comprising the vector of claim 1, and a carrier.

28. A composition, comprising the nucleic acid of claim 1, and a carrier.

29. A composition, comprising the vector of claim 13, and a carrier.

30. A host cell, transfected with the construct of claim 12.

31. A host cell, transfected with the vector of claim 13.

32. A host cell, transfected with the vector of claim 25.

33. A composition, comprising the host cell of claim 30, and a carrier.

34. An insulin-dependant diabetes mellitus diagnostic kit, comprising
the probe of claim 8; and
instructions for its use.

35. The kit of claim 34, further comprising a carrier for the probe.

36. An isolated polypeptide, encoded by the polynucleic acid of claim 1.

37. The polypeptide of claim 36, comprising SEQ ID NO 7.

38. The polypeptide of claim 36, obtained by a method comprising
culturing the host cell of claim 30 in an expression medium under conditions effective to express the encoded polypeptide; and
allowing the polypeptide to accumulate.

39. The polypeptide of claim 38, further purified by separation from the medium and the cells.

40. A method of producing a polypeptide, comprising
culturing the host cell of claim 30 in an expression medium under conditions effective to express the encoded polypeptide; and
allowing the polypeptide to accumulate.

41. The method of claim 40, further comprising separating the polypeptide from the medium and the cells.

42. A method of producing a polypeptide, comprising
culturing a host cell with the vector of claim 1 under conditions effective to transfect the cell with the vector;
culturing the transfected host cell in an expression medium under conditions effective to express the encoded polypeptide; and
allowing the polypeptide to accumulate.

43. The method of claim 42, further comprising separating the polypeptide and the cells.

* * * * *

UNITED STATES PATENT AND TRADEMARK OFFICE
CERTIFICATE OF CORRECTION

PATENT NO. : 5,763,591
DATED : June 9, 1998
INVENTOR(S) : Hiroo Toyoda and Bent Formby It is certified that error appears in the above-identified patent and that said Letters Patent is hereby corrected as shown below:

Column 2, line 48, change "α" into --β--.

Column 2, line 61, change "α" into --β--.

Column 14, line 35, change "420" into --42--.

Column 18, line 38, change "640" into --64--.

Column 18, line 43, change "CDNA" into --cDNA--.

Column 18, line 47, change "CDNA" into --cDNA--.

Column 18, line 49, change "640" into --64--.

Column 18, line 51, change "640" into --64--.

UNITED STATES PATENT AND TRADEMARK OFFICE
CERTIFICATE OF CORRECTION

PATENT NO. : 5,763,591
DATED : June 9, 1998
INVENTOR(S) : Hiroo Toyoda and Bent Formby It is certified that error appears in the above-identified patent and that said Letters Patent is hereby corrected as shown below:

Column 26, line 62, after "mellitus" insert -- (IDDM)--.

Signed and Sealed this

Second Day of March, 1999

*Attest:*

Q. TODD DICKINSON

*Attesting Officer*   Acting Commissioner of Patents and Trademarks